(12) United States Patent
Li et al.

(10) Patent No.: US 7,933,730 B2
(45) Date of Patent: Apr. 26, 2011

(54) METHOD AND SYSTEM FOR RESTORATION OF A NAVIGATION DATA LOSS IN IMAGE-GUIDED NAVIGATION

(75) Inventors: Dun Alex Li, Salem, NH (US); Daniel Eduardo Groszmann, Cambridge, MA (US)

(73) Assignee: General Electric Co., Schenectady, NY (US)

( * ) Notice: Subject to any disclaimer, the term of this patent is extended or adjusted under 35 U.S.C. 154(b) by 616 days.

(21) Appl. No.: 11/614,699

(22) Filed: Dec. 21, 2006

(65) Prior Publication Data
US 2008/0154526 A1 Jun. 26, 2008

(51) Int. Cl.
*G06F 19/00* (2011.01)
(52) U.S. Cl. ............ 702/94; 702/95; 702/104; 702/134; 702/152; 702/153; 324/207.16; 324/207.18; 324/207.19; 324/207.26; 342/463; 600/407; 600/424; 600/427; 600/429
(58) Field of Classification Search ............... 702/94–95, 702/104, 152–153, 134; 324/207.16, 207.19, 324/207.18, 207.26; 342/463; 600/407, 600/424, 427, 429, 130
See application file for complete search history.

(56) References Cited

U.S. PATENT DOCUMENTS

| | | | |
|---|---|---|---|
| 6,470,207 B1 * | 10/2002 | Simon et al. | 600/426 |
| 6,490,475 B1 | 12/2002 | Seeley et al. | |
| 2007/0078334 A1 * | 4/2007 | Scully et al. | 600/424 |

OTHER PUBLICATIONS

Livyatan et al."Robust Automatic C-Arm Calibration for Flouroscopy-Based Navigation: A Practical Approach," pp. 60-68; 2002.*
Disclosed Anonymously. "Method of Seed Estimation for Electromagnetic Tracker using a Priori Information." IP.com No. IPCOM000126878D, Aug. 5, 2005.

* cited by examiner

*Primary Examiner* — Sujoy K Kundu (57) ABSTRACT

A method for restoring navigation failure information in a fluoroscopy-based imaging system is disclosed. The method includes obtaining a plurality of receiver navigation information using a calibration target rigidly attached to a supporting member of the imaging system. The calibration target may include a plurality of receivers providing navigation information and the supporting member may be a C-arm. The method identifies a navigation failure and corresponding to the navigation failure a calibrated receiver navigation information is generated. The calibrated receiver navigation information is generated using a calibration information and a C-arm imaging position obtained during navigation failure. A receiver navigation information corresponding to the navigation failure is estimated using the calibrated receiver navigation information, and a transmitter navigation information. Also disclosed is a restoration unit for restoring navigation failure information in a fluoroscopy-based imaging system and a fluoroscopic imaging system using the restoration unit.

20 Claims, 7 Drawing Sheets

METHOD AND SYSTEM FOR RESTORATION OF A NAVIGATION DATA LOSS IN IMAGE-GUIDED NAVIGATION

FIELD OF THE INVENTION

The present invention generally relates to imaging and image-guided navigation. In particular, the present invention relates to a system and method for restoration of navigation data loss in imaging and image-guided navigation operations.

BACKGROUND OF THE INVENTION

Medical practitioners, such as doctors, surgeons, and other medical professionals, often rely upon technology when performing a medical procedure, such as image-guided surgery or examination. A tracking or navigation system may provide positioning information for a medical instrument with respect to the patient or a reference coordinate system, for example. A medical practitioner may refer to the navigation system to ascertain the position of the medical instrument when the instrument is not within the practitioner's line of sight. A tracking system may also aid in pre-surgical planning.

The tracking or navigation system allows the medical practitioner to visualize the patient's anatomy and track the position and orientation of the instrument. The medical practitioner may use the tracking system to determine when the instrument is positioned in a desired location or at a desired orientation. The medical practitioner may locate and operate on a desired or injured area while avoiding other structures. Increased precision in locating medical instruments within a patient may provide for a less invasive medical procedure by facilitating improved control over smaller instruments having less impact on the patient. Improved control and precision with smaller, more refined instruments may also reduce risks associated with more invasive procedures such as open surgery.

Tracking systems can include ultrasound, inertial position, optical, or electromagnetic tracking systems, for example. Electromagnetic (EM) tracking systems may employ coils as receivers and transmitters. Typically, an EM tracking system is configured using an industry-standard coil architecture (ISCA). ISCA uses three co-located orthogonal, quasi-dipole transmitter coils and three co-located quasi-dipole receiver coils. Other systems may use three large, non-dipole, non-co-located transmitter coils with three co-located quasi-dipole receiver coils. Another tracking system architecture uses an array of six or more transmitter coils spread out in space and one or more quasi-dipole receiver coils. Alternatively, a single quasi-dipole transmitter coil may be used with an array of six or more receivers spread out in space.

Tracking accuracy, navigable range, and metal tolerance are three challenging and often conflicting concerns to be addressed when designing an EM tracking system. For fluoroscope-based two-dimensional image navigation applications, both tracking volume (e.g., transmitter to receiver distance) and metal distortion can be managed by users via adjustment of an image intensifier with a calibration target attachment (e.g., fiducial markers, EM receiver, and shield) closer to a patient anatomy where a transmitter is usually placed.

For three-dimensional image navigation applications, however, the transmitter-to-calibration target receiver distance varies as the C-arm is rotated to different positions. Users generally have limited control of transmitter placements depending on various clinical applications to fulfill a tracker range requirement. As the position of the C-arm keeps changing during a spin, there is a chance of losing the tracker data due to table interference or due to the transmitter going out of range.

In an example, the navigation coverage may be increased by increasing the tracker range. However increasing the tracker range generally requires an increase of the transmitter size and results in significant hardware changes. Also, this solution will not solve the problem of EM interference caused by the presence of surgical or patient tables, which are generally made with significant amounts of metals.

Alternatively, the tracker field of view may be increased by distributing an array of EM receivers on the X-ray detector. The table interference can be minimized to some degree by using the least distorted tracker readings obtained from the sensor with the largest distance from the table at a 3D rotation position. This, however, may increase system complexity since it requires additional A/D electronics for multiple channel signal acquisition, and a complicated computer algorithm for determining optimal sensor outputs.

Thus there exists a need to restore the tracking information lost in a three-dimensional (3-D) image acquisition spin. It would be desirable to provide a system and method for automatically restoring tracking information or navigation data loss in an image guided system.

SUMMARY OF THE INVENTION

The above-mentioned shortcomings, disadvantages and problems are addressed herein which will be understood by reading and understanding the following specification.

One embodiment of the present invention provides a method for restoring navigation failure information in a fluoroscopy-based imaging system. The method includes: obtaining a plurality of receiver navigation information using a calibration target rigidly attached to a supporting member of the imaging system, said calibration target including a plurality of receivers providing navigation information and the supporting member including a C-arm; identifying a navigation failure; determining a calibrated receiver navigation information using a calibration information and a C-arm imaging position obtained during navigation failure; and estimating a receiver navigation information corresponding to the navigation failure using the calibrated receiver navigation information, and a transmitter navigation information.

In another embodiment, a unit for restoring navigation failure information in a navigation system is provided. The system includes: a calibration target rigidly attached to a fluoroscopy C-arm in the navigation system, said calibration target including a plurality of receivers providing receiver navigation information; an identifier associated with the receiver for identifying a navigation failure information; and a connector for providing receiver navigation information, transmitter navigation information, navigation failure information and selected C-arm position to a processor. In this system, the processor is configured for generating receiver navigation failure information corresponding to the navigation failure information, based upon a calibration information, C-arm position and a transmitter navigation information.

In yet another embodiment, a computer program provided on one or more computer readable media for restoring navigation failure information in a fluoroscopy based navigation system is disclosed. The computer program includes: a routine for obtaining a calibrated receiver navigation information using a calibration information and a C-arm position; a routine for obtaining navigation failure information; and a routine for estimating receiver navigation failure information corresponding to the navigation failure information based on the calibrated receiver navigation information and transmitter navigation information.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the invention. The following detailed description is, therefore, not to be taken as limiting the scope of the invention.

In various embodiments, a method of restoring tracking information in a fluoroscopy imaging system is disclosed. In an embodiment, the imaging system may be an imaging system used in cardiovascular applications, 3D imaging applications, or 2D imaging applications. In certain embodiments, the imaging system includes a mobile C-arm, L-arm, O-arm or similar device integrated with a flat panel detector (FPD) and an EM tracking system having both 2D and 3D surgical navigation capabilities. In an embodiment, the imaging system is a fluoroscopy-based imaging device, such as a Computer tomography imaging system, a magnetic resonance imaging system, etc. However, the application of the method of restoration disclosed herein need not be limited to the above mentioned imaging systems and applications.

While the present technique is described herein with reference to medical imaging applications, it should be noted that the invention is not limited to this or any particular application or environment. Rather, the technique may be employed in a range of applications, such as baggage and parcel handling and inspection, part inspection and quality control, and so forth, to mention but a few other applications outside medical.

The present invention also provides a restoration unit for automatic restoration of tracking or navigation information loss and an imaging system incorporating the restoration unit.

Figure 1:
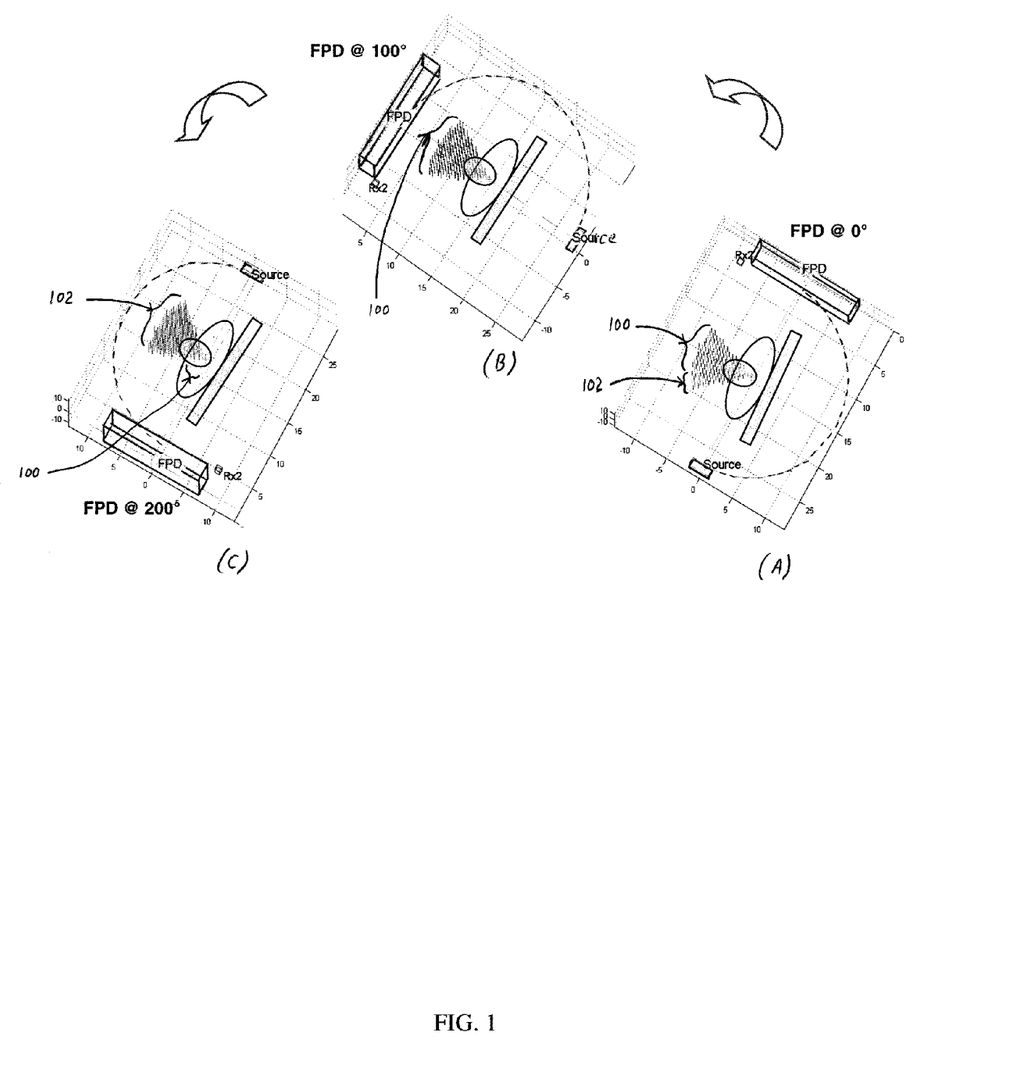
FIG. 1 illustrates a three dimensional image acquisition spin of a patient anatomy.

FIG. 1 illustrates a three dimensional image acquisition spin of a patient anatomy. The figure is explained with reference to a flat panel detector (FPD) imaging system rotating around a patient anatomy centered on a surgical table. Part A of FIG. 1 shows the FPD scan position at 0 degrees, part B shows the FPD scan position at 100 degrees, and part C shows the FPD scan position at 200 degrees. In an example, the patient anatomy in the figure is subjected to spine thoracic application. The array of dots about the patient anatomy represents the possible locations for transmitter placements during a 3-D spin. As shown, the dots 100 represent clinical volume within tracking range of a C-arm in the imaging system and the dots 102 represent the clinical volume outside the clinical volume range. The ratio of the clinical volume within the tracking range over the total number of transmitter positions is termed as navigation coverage percentage. Thus it is clear that the navigation coverage is limited in a 3-D spin, by the degree of rotation of the flat panel detector. Hence there exists a possibility of losing tracker data or tracking information or navigation information whenever the transmitter position is outside the navigation coverage area. In FIG. 1 when the flat panel detector (FPD) is at 100 degree (part B), it is to be noted that the navigation coverage is 100% (illustrated in the figure by all of the dots being dots 100). When the FPD is at 200 degree (part C), the navigation coverage is very low and is about 3% (illustrated in the figure by only a small percentage of the dots being dots 100). When the FPD is at 0 degree (part A), the navigation coverage is about 88% (illustrated in the figure by most but not all of the dots being dots 100). But it is to be noted that at 0 degree the receiver positioned on the FPD is located below the patient table and this may cause tracking information loss due to the interference from the surgical table. For 3D image navigation applications, however, the transmitter to calibration target receiver distance, which limits the operating range of C-arm, varies as the C-arm is rotated to different positions. Thus during a 3-D spin of a patient anatomy, the tracking information is lost due to operating range limitations of the C-arm and due to the metal interference of the surgical table.

Figure 2:
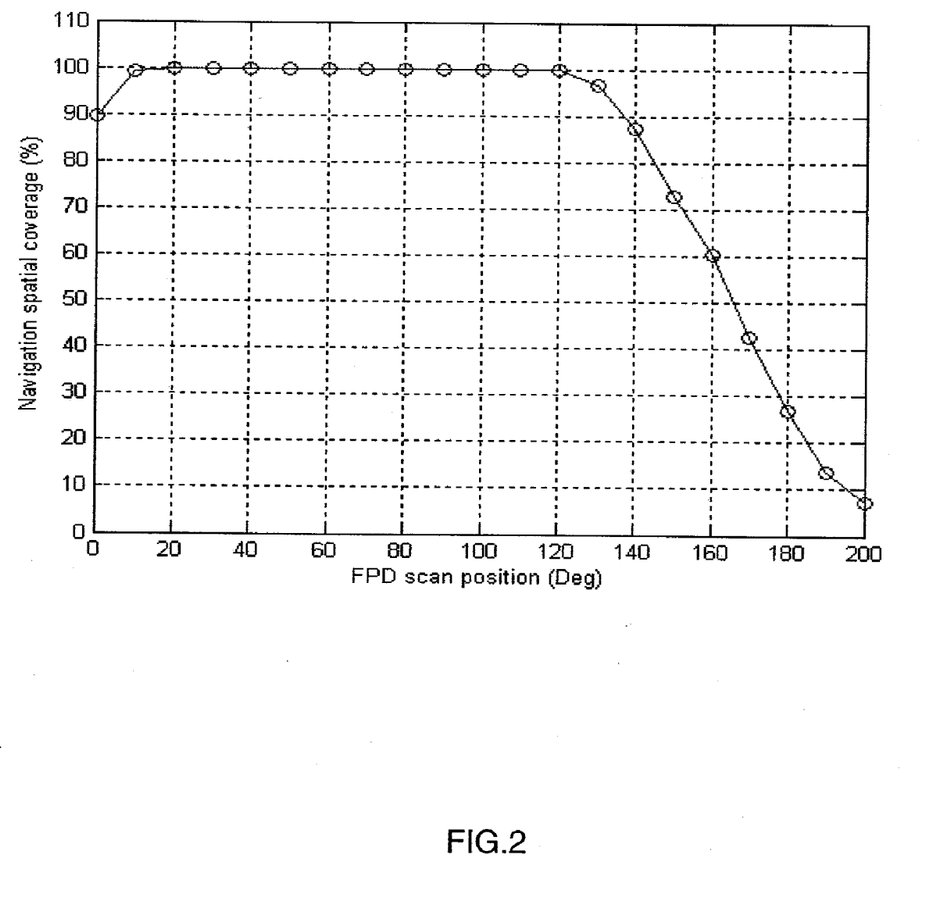
FIG. 2 illustrates a navigation coverage of a C-arm during a three dimensional spin.

FIG. 2 is a graph illustrating navigation coverage of a C-arm during a three dimensional spin. The figure shows the navigation coverage percentage taken for 0-200 degrees in a spine thoracic application using a flat panel detector. It has been shown that only 50% (i.e., from 20-120 degree) of the 200 degree spin positions have full navigation coverage of a prospective clinical volume. The rest of the spin (i.e., less than 20 degrees or more than 120 degrees) have less than full navigation coverage of a prospective clinical volume. Thus the impact of tracking information loss can be high in navigation of two-dimensional images acquired during a three-dimensional spin.

Figure 3:
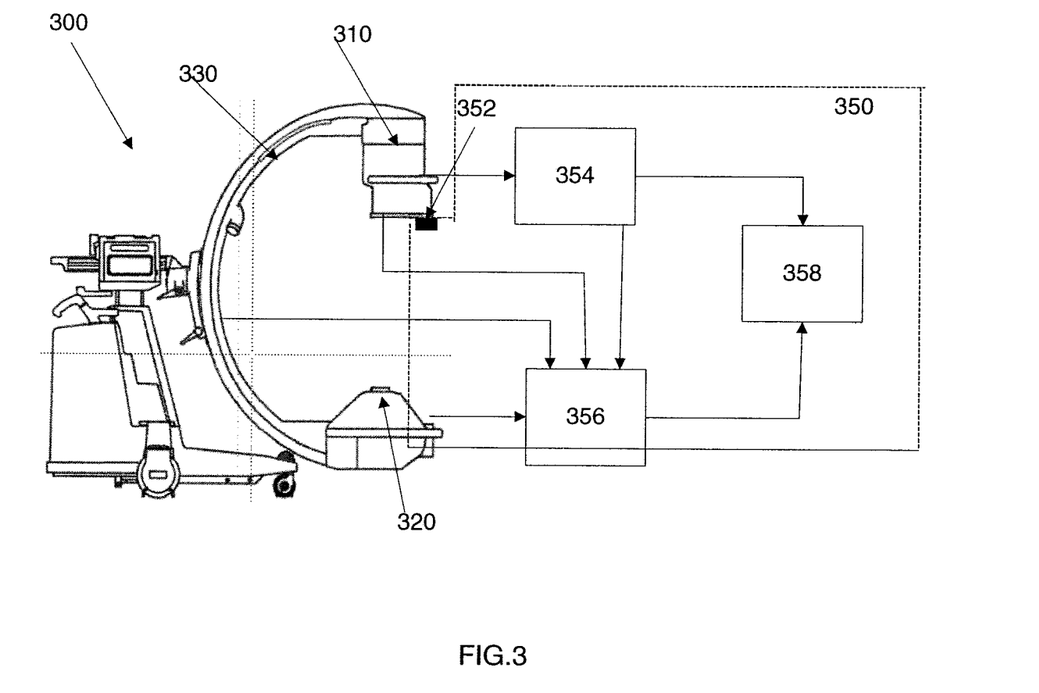
FIG. 3 is a schematic diagram of an imaging system implementing a restoration unit as disclosed in an embodiment of the invention.

FIG. 3 is a schematic diagram of an imaging system implemented with a unit for restoring navigation failure information as disclosed in an embodiment of the invention. In an embodiment, the imaging system 300 may be a fluoroscopy-based imaging device, such as a Computer tomography imaging system, a magnetic resonance imaging system, or another type or modality of medical imaging device.

The imaging system 300 includes an imager 310, a source 320 and a structural support member 330. The imager 310 may be an X-ray detector, for example. The detector may be a flat panel detector or an image intensifier detector. The source 320 may be an X-ray generator, such as an X-ray tube, for example. The structural support member 330 may be a C-arm supporting the imager 310 and source 320 at opposite ends, as illustrated in FIG. 3. However, support member 330 may also be an L-arm, O-arm and/or other structure supporting the imager 310 and source 320. For example, the imager 310 may be mounted at a first end of the structural support member 330 opposite the source 320, which is mounted at a second end of structural support member 330. The support member 330 moves about a patient or other object to produce two dimensional projection images of the patient from different angles. The patient or object remains positioned between the imager 310 and the source 320, and may, for example, be situated on a table or other support, although the patient/object may move.

In an embodiment, a transmitter is affixed on the patient anatomy of surgical interest. A receiver is mounted on an instrument (not shown), such as a probe or surgical tool, or with respect to a patient or other object. The instrument may be rigid, allowing the receiver to be fixed at a known or convenient position, such as on its handle. Alternatively, the tool may be a flexible tool, such as a catheter, flexible endoscope or an articulated tool, for example. In the latter cases, the receiver (or transmitter) is preferably a small, localized element positioned in or at the operative tip of the tool to track coordinates of the tip within the body of the patient. The transmitter and receiver are sensors determining the navigation information and the terms may be inter-changed.

In an embodiment a restoration unit 350 for restoring tracking data loss or navigation information, is provided with the imaging system 300 for restoring the tracking data loss. The terms tracking data loss, missing tracking information, navigation information loss, navigation failure information, etc., convey the same meaning and each indicates a navigation failure. The restoration unit 350 comprises a calibration target 352, attached to the supporting member 330, for example, C-arm of the imaging system. For example, the calibration target 352 may be attached to the imager or detector located on the C-arm 330. Reference to the C-arm is only for explanation, and the supporting member may alternatively be an L-arm, O-arm or similar supporting member. The calibration target 352 may include fiducial markers, EM receiver, shield, etc., which are rigidly fixed to the C-arm 330 of the imaging system 300. In an embodiment, the calibration target 352 includes a plurality of receivers providing receiver navigation information. The calibration target 352, referred to as a receiver hereinafter, provides receiver navigation information with respect to the transmitter. Reference to a receiver is only for explanation, and the calibration target 352 need not be limited to the receiver. The receiver navigation information includes position and orientation of the receiver with respect to transmitter within a valid tracking range of operation. The valid tracking range may be a predefined range of distance measured between the transmitter and the receiver during a 3-D C-arm spin, based on the navigation coverage. In an example the preferred distance between the receiver and the transmitter is 3 to 18 inches, although other distances between the receiver and the transmitter may be used. The receiver and the transmitter act together and generate a navigation information. During a tracking or navigation failure, there will not be any receiver navigation information available. However the data corresponding to the position of the C-arm is being tracked, and using the C-arm position information during the tracking failure, a calibrated receiver navigation information is generated and the missing tracking information is restored.

An identifier 354 is provided for identifying the receiver tracking failure information. The tracking failure or navigation failure may be due to the movement of the transmitter position outside the tracking volume, or due to table interference, when the position of the receiver is below the patient table. The identifier 354 identifies the navigation failure information or missing of the tracking information. In an embodiment, the identifier 354 is a program that identifies the missing of the tracker information or a connection that identifies a signal loss corresponding to the navigation information.

A connector 356 is provided for coupling the imaging system 300 with the restoration unit 350. The connector 356 is configured to collect the navigation information from the receiver and the transmitter, and to provide the same to a processor 358. Also the connector 356 may receive the navigation failure information from the identifier 354 and provide it to the processor 358. The connector 356 further collects the imaging position information of the C-arm 330 in the imaging system 300 and provides the same to the processor 358. In a 3-D image sweep, the imaging position of the C-arm 330 and the distance between the transmitter and the receiver changes continuously. In different embodiments of the present invention, the connector 356 is a wired cable, a wireless connection or a program that identifies tracking information from the receiver and transmitter, C-arm position, tracking failure information, etc.

The connector 356 provides the tracking information, tracking failure information, C-arm imaging position information, etc., to the processor 358. The processor 358 is configured for restoring the navigation or tracking failure information.

In an embodiment, the processor 358 is configured for estimating a receiver tracking information corresponding to the receiver navigation failure information using a calibrated receiver navigation information and a transmitter navigation information. The calibrated receiver navigation information is generated based on a calibration information corresponding to a C-arm position.

In an embodiment the processor 358 is further configured for generating calibration information using a plurality of receiver navigation information with respect to different C-arm positions. A plurality of receiver navigation information is obtained during a 3-D image spin and the acquisition of the receiver navigation information and images is synchronized with the C-arm imaging position. A C-arm imaging position is obtained. Based on the receiver tracking information a rotation center is estimated. A world coordinate system (WCS) is defined at the rotation center. The receiver navigation information is re-computed in the world coordinate system. This information is called calibration information and the calibration information is obtained corresponding to a plurality of C-arm imaging positions and is stored in the form of a lookup table. The lookup table may be stored in a memory, which is associated with the processor 358.

The processor 358 is further configured for restoring the receiver navigation failure information using the transmitter navigation information, C-arm position and the calibrated receiver navigation information.

In an embodiment, the positions of receiver and transmitter attachment on the C-arm, instrument, or patient anatomy are inter-changeable.

In an embodiment, the imaging system 300, such as a fluoroscope system, operates with the imager 310 positioned opposite the X-ray source or generator 320. In some imaging systems, the imager 310 is fixed overhead and the source 320 is located below a patient support. However, in other systems such as shown in FIG. 3, the imager or detector 310 and source 320 may be connected by the structural support member 330, such as a C-arm, that allows movement of the imager 310 and source 320 about the patient or object being imaged so that the C-arm may be positioned to produce x-ray views from different angles or perspectives. In such C-arm devices, the imaging beam generally diverges at an angle, the relative locations and orientations of the imager 310 and source 320 vary with position due to structural flexing and mechanical looseness, and the position of both the imager 310 and the source 320 with respect to the patient and/or a tool which it is desired to track may also vary in different shots. Thus the C-arm in the imaging device may be a mobile C-arm.

Figure 4A:
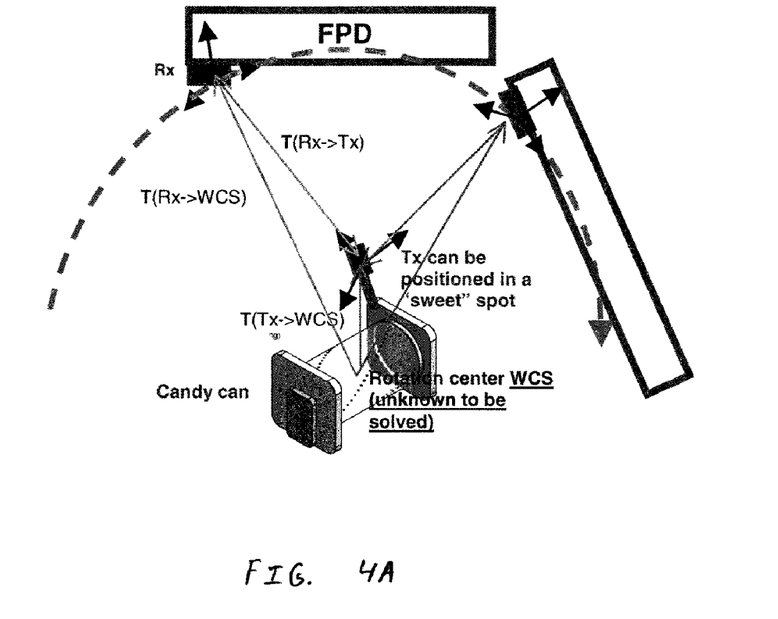
FIGS. 4A and 4B illustrate a method of restoration as described in an embodiment of the invention using a fluoroscopy based imaging system.
Figure 4B:
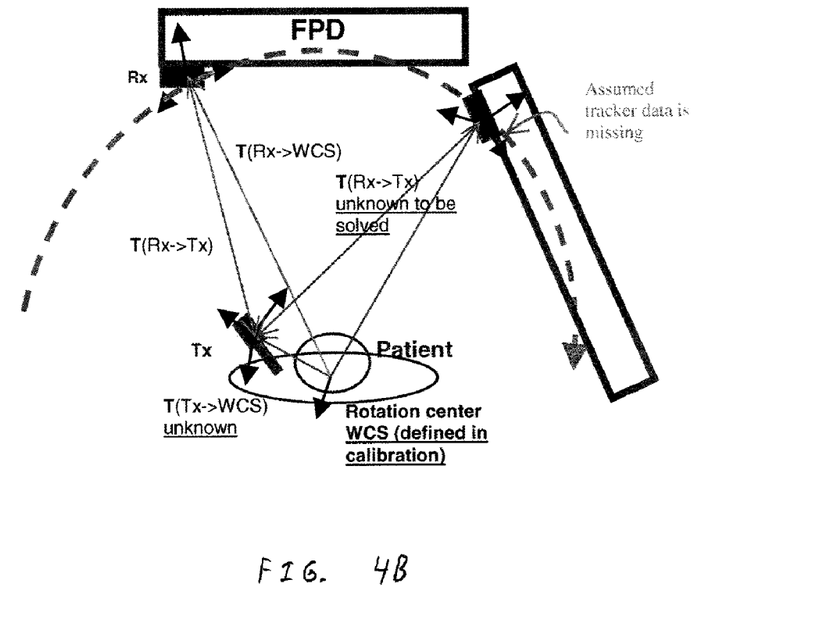

FIGS. 4A and 4B illustrate a method of restoration as described in an embodiment of the invention. In some specific navigation applications such as mobile C-arm tracking systems, the receiver is permanently attached to a C-arm and is moved together with the C-arm on a well-controlled spatial path. In the calibration process, the receiver navigation information is correlated with known C-arm position information. FIG. 4A illustrates a calibration step of the restoration method. As illustrated in FIG. 4A, a receiver (Rx) is rigidly attached to a flat panel detector (FPD), and a transmitter (Tx) is affixed to a calibration phantom and remains in the same location and pose with respect to the world coordinate system (WCS) during a 3D spin. A series of receiver navigation information is obtained during the 3-D spin. The receiver navigation information includes position and orientation of the receiver Rx with respect to the transmitter Tx within a predefined range of distance measured between the transmitter Tx and the receiver Rx during a 3-D C-arm spin. The receiver navigation information (or tracker data acquisition) needs to be synchronized with image acquisition or the C-arm imaging position. A plurality of receiver navigation information T(Rx->Tx) is obtained. The receiver navigation information should be within the range limit of the distance between the transmitter Tx and the receiver Rx. Using the plurality of the receiver navigation information, a rotation center is defined such that the C-arm motion is defined in a perfect circle. A world coordinate system is then defined at the rotation center. The receiver navigation information is re-computed T(Rx->WCS) at the world coordinate system. The recomputed receiver navigation information or calibration information is obtained corresponding to a plurality of C-arm imaging positions. A plurality of C-arm imaging positions is obtained in a 3-D spin and corresponding to each C-arm position a calibration information is generated. The plurality of transmitter navigation information is obtained. The transmitter navigation information is also defined at the world coordinate system T(Tx->WCS).

FIG. 4B illustrates the acquisition step during the fluoro-image acquisition during restoration method. Assume a navigation information is missing or the identifier identifies a receiver navigation failure information. The C-arm position corresponding to the receiver navigation failure information is obtained. The position of the C-arm is tracked for each spin and hence the C-arm position information is easily available. Based on the C-arm position and using the step illustrated in FIG. 4A, a calibration information T(Rx→WCS) is calculated. Alternatively, a calibration information is obtained from a lookup table having calibration information corresponding to different C-arm positions. Using the calibration information and the C-arm position, a calibrated receiver information is obtained corresponding to the navigation failure. This is achieved using the C-arm position corresponding to the receiver navigation failure information. A plurality of transmitter navigation information T(Tx->WCS) is obtained. The transmitter navigation information is obtained corresponding to the receiver navigation information falling within the valid tracker range T(Rx->Tx) and an average best fit position is calculated for transmitter navigation. The transmitter navigation information is defined in the world coordinate system. Using this transmitter navigation information, the transmitter navigation information corresponding to the receiver navigation failure information is obtained. Using the calibrated receiver navigation information obtained corresponding to the C-arm position and the transmitter navigation information corresponding to the navigation failure information T(Rx->Tx) is estimated. Thus the unknown missing navigation information is correlated with the known C-arm imaging position.

Figure 5:
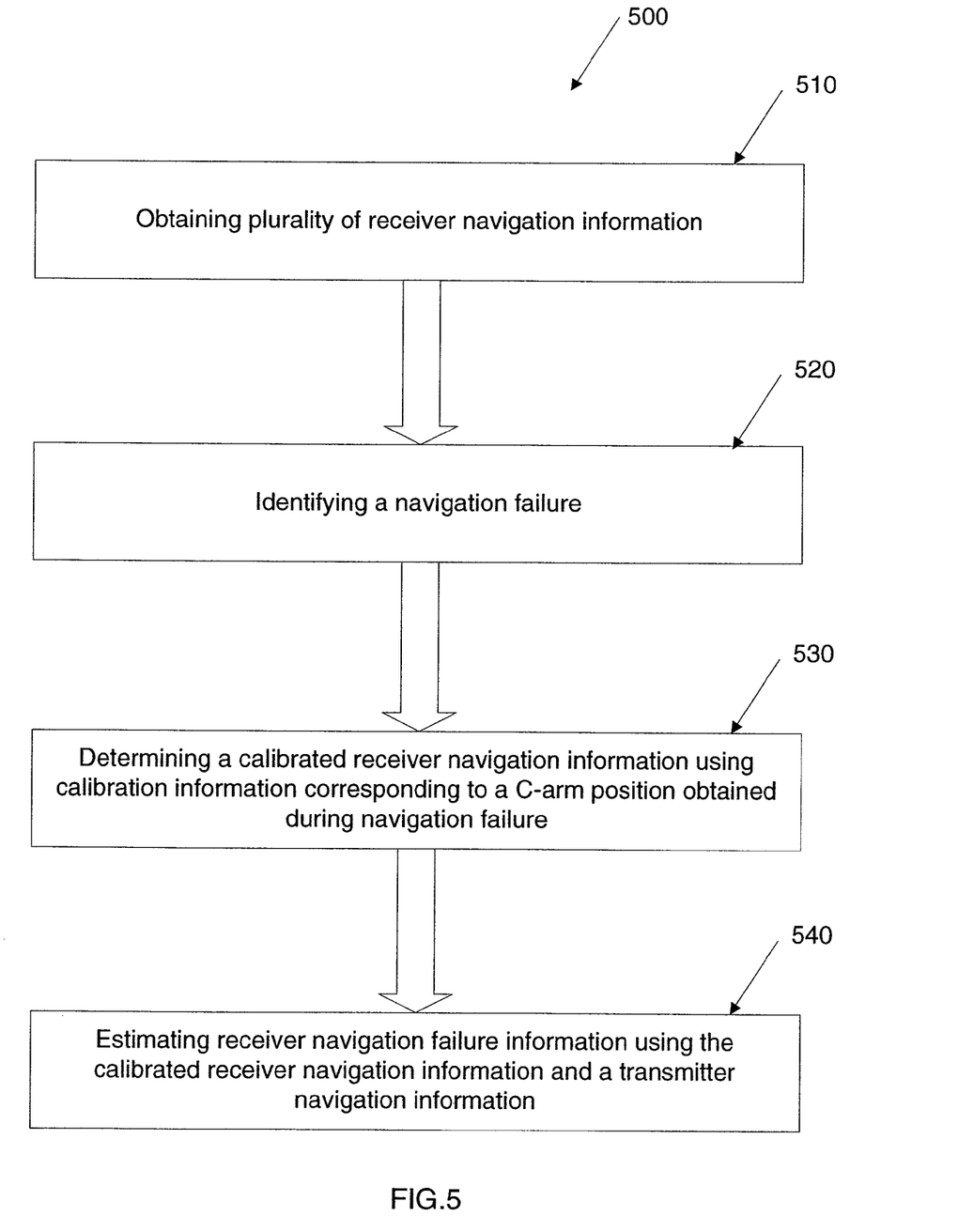
FIG. 5 is a high-level flowchart illustrating a method of restoration in an imaging system as disclosed in an embodiment of the invention.

FIG. 5 is a high level flowchart illustrating the method of restoration in an imaging system in accordance with one embodiment of the invention. The method of restoration 500, is described with reference to a fluoroscopy based imaging system. At step 510, a plurality of receiver navigation information is obtained. The receiver navigation information includes position and orientation of the receiver with respect to the transmitter within a predefined range of distance measured between the transmitter and the receiver. The receiver navigation information is obtained using a calibration target. The calibration target is configured to be an array of radio opaque fiducials or receivers arranged for use in image calibration for an imaging system. At step 520, a navigation failure is identified. A receiver navigation failure information is obtained corresponding to each navigation failure. The receiver navigation failure information indicates the absence of receiver navigation information corresponding to a particular C-arm position. The navigation failure may occur due to tracking range limits or table interference. At step 530, a calibrated receiver navigation information is obtained. The calibrated receiver navigation information is generated using a C-arm position obtained during the navigation failure. Based on the C-arm position information, corresponding calibrated receiver navigation information is obtained. The calibrated navigation information is obtained using a calibration information. The various steps involved in obtaining the calibration information are described in detail in FIG. 7. At step 540, a receiver navigation failure information is estimated corresponding to navigation failure. This is achieved using the calibrated receiver navigation information corresponding to a C-arm position, which is obtained during the navigation failure, and the transmitter navigation information in the world coordinate system, obtained corresponding to the navigation failure. The steps involved in estimating the receiver failure information will be explained in detail in FIG. 6.

Figure 6:
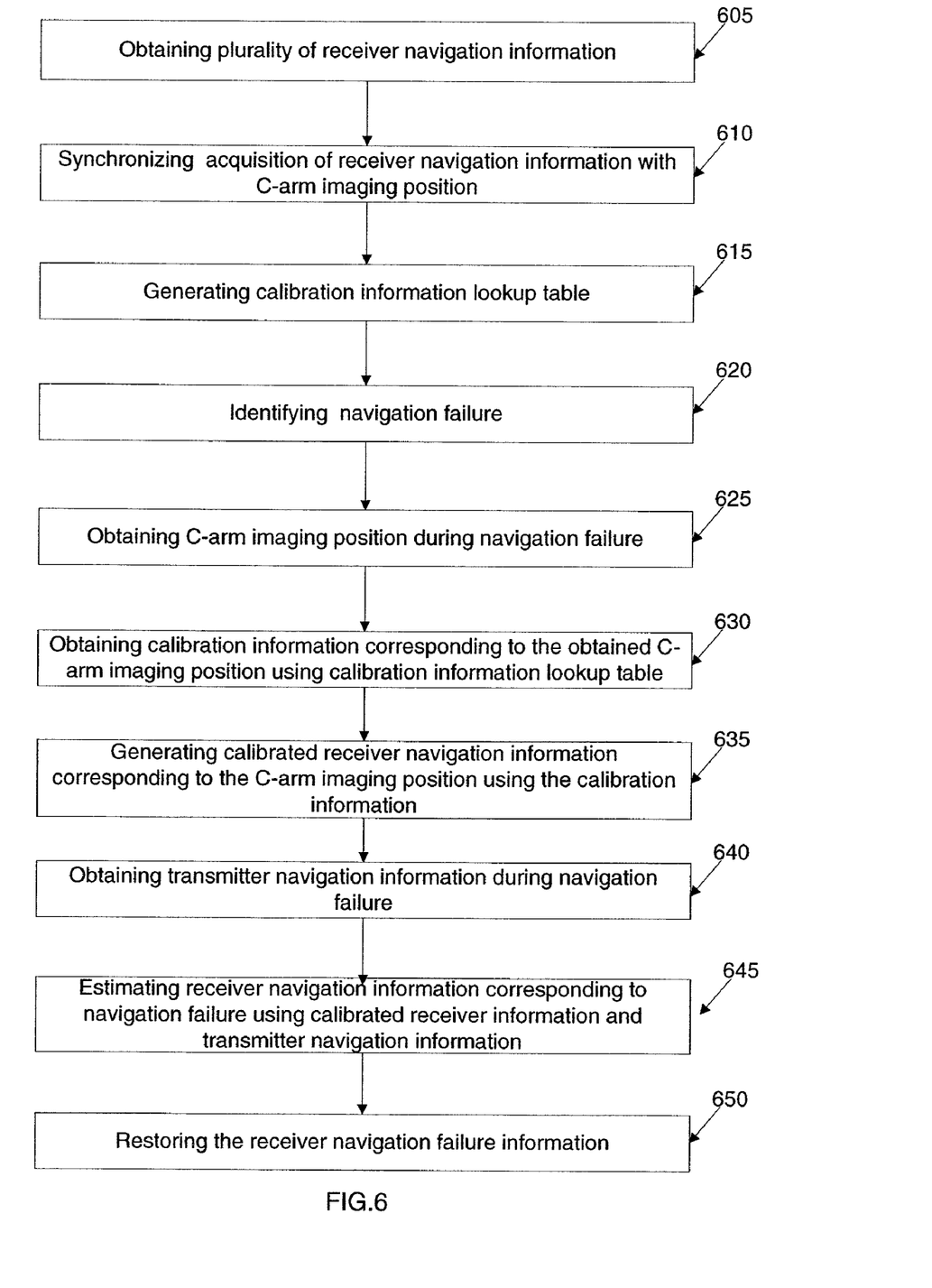
FIG. 6 is a flowchart depicting exemplary steps of the method of restoration illustrated in FIG. 5.

FIG. 6 is a flowchart describing, in greater detail, exemplary steps of the method of restoring tracker data in an imaging system illustrated in FIG. 5. At step 605, a plurality of receiver navigation information is obtained. The receiver navigation information includes position and orientation of the receiver with respect to the transmitter within a predefined range of distance measured between the transmitter and the receiver during a 3-D C-arm spin. At step 610, the acquisition of the images and navigation information is synchronized with the movement of the C-arm. At step 615, a calibration information is generated based on the plurality of the receiver navigation information. Corresponding to different C-arm positions, calibration information is calculated and is stored in the form of a lookup table. The various steps involved in generation of calibration information are explained using FIG. 7. At step 620, a navigation failure is identified. This is done by obtaining a receiver navigation failure information corresponding to the navigation failure. Whenever there is a missing of receiver navigation information corresponding to a C-arm imaging position, a receiver navigation failure information is generated. At step 625, the C-arm imaging position during the receiver navigation failure is obtained. At step 630, the calibration information corresponding to the obtained C-arm position is determined. The calibration information may be obtained from the lookup table generated by Step 615. At step 635, from the C-arm position and the corresponding calibration information, using a higher order interpolation or similar equivalent scheme, a calibrated receiver navigation information is generated. At step 640, transmitter navigation information is obtained. The transmitter navigation information includes the position and orientation information of the transmitter with respect to the receiver during the navigation failure. A World coordinate system for transmitter navigation information is defined using the transmitter navigation information. At step 645, receiver navigation information corresponding to navigation failure is obtained using the calibrated receiver navigation information obtained by step 635 and the transmitter navigation information obtained by step 640. This is achieved by using a coordinate transformation. At step 650, the receiver navigation information corresponding to navigation failure is restored using the receiver navigation information estimated in step 645.

Figure 7:
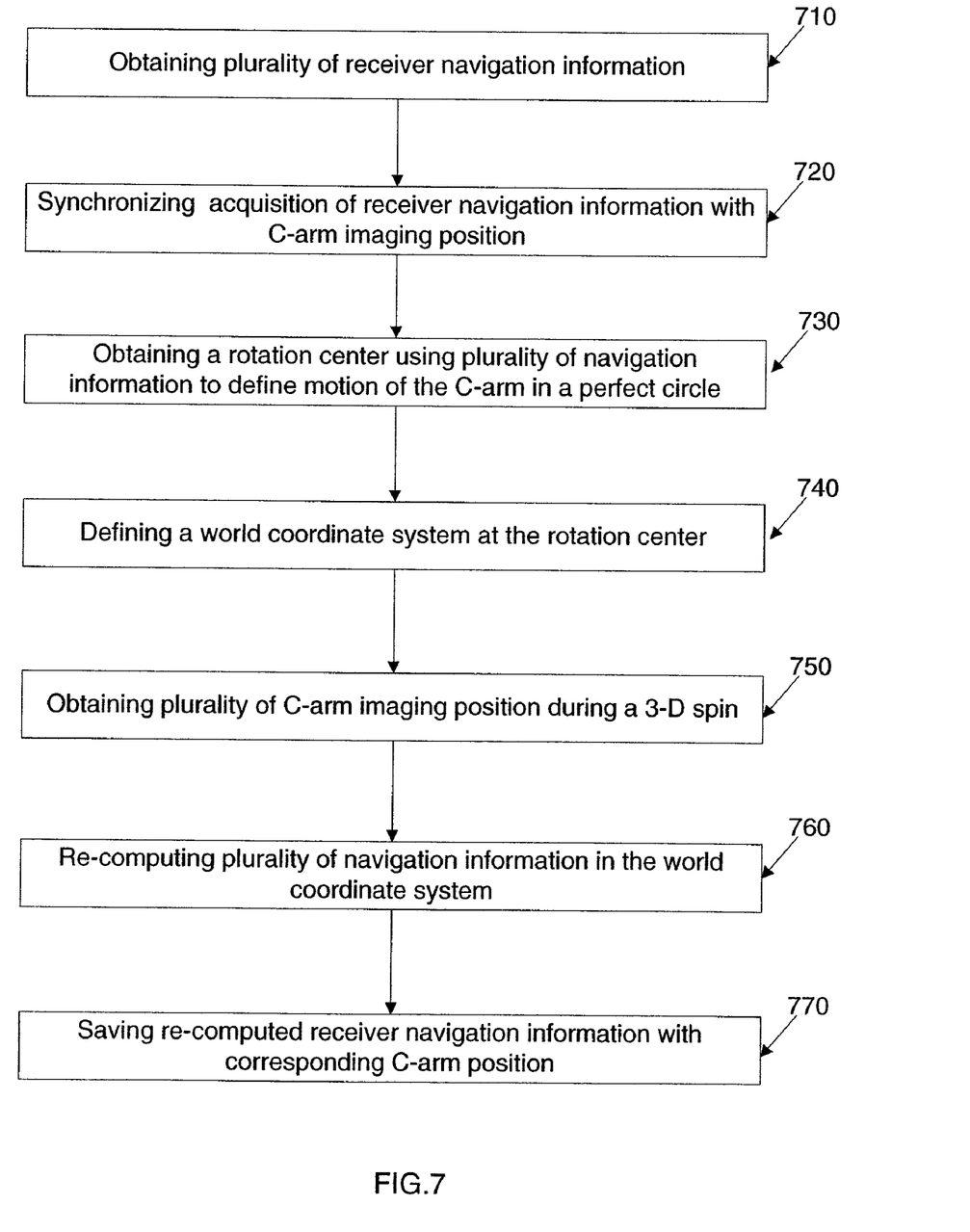
FIG. 7 is a flowchart describing, in greater detail, exemplary steps of a method of generating calibration information as described in an embodiment of the invention.

FIG. 7 illustrates a method of obtaining calibration information as disclosed in an embodiment of the invention. At step 710, a plurality of receiver navigation information is obtained. At step 720, the image and receiver navigation information acquisition is synchronized with movement of the C-arm. At step 730, a rotation enter is defined using a plurality of navigation information for defining the movement of the C-arm in a perfect circle. At step 740, a world coordinate system is defined at the rotation center. At step 750, a plurality of C-arm imaging positions are obtained during a 3-D spin. At step 760, the receiver navigation information is calculated in world coordinate system, corresponding to each C-arm imaging position. At step 770, the re-computed receiver navigation information or the calibration information is stored in a lookup table.

Thus various embodiments of the invention disclose a method and system for restoring a tracking or navigation information in an image guiding operation.

It should be noted that, although the flow charts provided herein show a specific order of method steps, it is understood that the order of these steps may differ from what is depicted. Also, two or more steps may be performed concurrently or with partial concurrence. It is understood that such variations are within the scope of the invention.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

What is claimed is:

1. A method for restoring navigation failure information in a fluoroscopy-based imaging system, comprising:
    (a) obtaining a plurality of receiver navigation information using a calibration target attached to a supporting member of the imaging system, said calibration target including a plurality of receivers providing navigation information and the supporting member including a C-arm;
    (b) identifying a navigation failure;
    (c) determining a calibrated receiver navigation information using a calibration information defined corresponding to each C-arm position and a C-arm imaging position obtained during the navigation failure;
    (d) estimating a receiver navigation information corresponding to the navigation failure by a coordinate transformation using the calibrated receiver navigation information, and a transmitter navigation information, the transmitter navigation information being selected corresponding to the receiver navigation information falling within a valid tracker range; and
    (e) restoring the navigation failure information using estimated receiver navigation information.

2. A method as in claim 1, further comprising, synchronizing acquisition of receiver navigation information with C-arm imaging position.

3. A method as in claim 1, wherein the receiver navigation information includes position and orientation of the receiver with respect to the transmitter within a predefined range of distance measured between the transmitter and the receiver during a three dimensional C-arm sweep and the transmitter navigation information includes position and orientation of the transmitter with respect to the receiver within a predefined range of distance measured between the transmitter and the receiver during a three dimensional C-arm spin.

4. A method as in claim 1, wherein the C-arm is a mobile C-arm.

5. A method as in claim 1, wherein positions of receiver and transmitter attachment on the C-arm, instrument, or patient anatomy are inter-changeable.

6. A method as in claim 1, wherein the step of determining calibration information comprises:
    (a) obtaining a plurality of receiver navigation information;
    (b) defining a rotation center using the receiver navigation information, for defining motion of the C-arm in a circle;
    (c) defining a world coordinate system at the rotation center;
    (d) obtaining a plurality of C-arm positions in the imaging system; and
    (e) re-computing plurality of receiver navigation information, corresponding to each C-arm position in the world co-ordinate system.

7. A method of claim 1, wherein the step of obtaining calibrated receiver information comprises: generating a higher order interpolation using the calibration information and the C-arm imaging position.

8. A method as in claim 1, wherein estimating a receiver navigation failure information comprises:
    (a) obtaining a C-arm position during navigation failure;
    (b) obtaining a calibrated receiver navigation information corresponding to the C-arm position; and
    (d) obtaining a plurality of transmitter navigation information with respect to the receiver in the world co-ordinate system, during a navigation failure.

9. A method as in claim 1, wherein estimating a receiver navigation failure information further comprising: restoring the receiver navigation failure information corresponding to the navigation failure based on a coordinate transformation using the transmitter navigation information and the calibrated receiver navigation information.

10. A method as in claim 1, wherein the fluoroscopy navigation system is configured to be a fluoroscopy C-arm imaging system, a computer tomography imaging system or a magnetic resonance imaging system.

11. A unit for restoring navigation failure information in a navigation system comprising:
    a calibration target attached to a fluoroscopy C-arm in the navigation system, said calibration target including a plurality of receivers providing receiver navigation information;
    an identifier associated with the receiver for identifying a navigation failure information; and
    a connector for providing receiver navigation information, transmitter navigation information, navigation failure information and selected C-arm position to a processor;
    wherein the processor is configured for generating receiver navigation failure information corresponding to the navigation failure information, based upon a calibration information, C-arm position and a transmitter navigation information by a coordinate transformation and for restoring the navigation failure information using estimated receiver navigation information.

12. A unit as in claim 11, wherein the receiver navigation information includes position and orientation of the receiver with respect to a transmitter within a predefined range of distance measured between the transmitter and the receiver during a three dimensional C-arm spin and the transmitter navigation information includes position and orientation of the transmitter with respect to the receiver within a predefined range of distance measured between the transmitter and the receiver during a three dimensional C-arm spin.

13. A unit as in claim 11, wherein the calibration target is configured to be an array of radio opaque fiducials or receivers arranged for use in image calibration for an imaging system.

14. A unit of claim 11, wherein the transmitter is attached to a fixture and is positioned maintaining predefined distance with the receiver.

15. A unit as in claim 11, wherein the processor is configured for generating calibration information using plurality of receiver navigation information corresponding to plurality of C-arm positions.

16. A unit as in claim 15, wherein the processor is further configured for restoring the receiver navigation failure information based on a coordinate transformation using the transmitter navigation information during navigation failure and the calibrated receiver navigation information.

17. A unit as in claim 11, wherein the image navigation system includes a fluoroscopy navigation imaging system.

18. A non-transitory computer readable medium containing computer instructions stored thereon for causing a computer processor to perform:
- a routine for obtaining a calibrated receiver navigation information using a calibration information and a C-arm position;
- a routine for obtaining navigation failure information;
- a routine for estimating receiver navigation failure information corresponding to the navigation failure information based on the calibrated receiver navigation information and transmitter navigation information by a coordinate transformation; and
- a routine for restoring the navigation failure information using estimated receiver navigation information.

19. The non-transitory computer readable medium of claim 18, wherein the routine for obtaining calibrated receiver navigation information comprising: a routine for obtaining a calibration information corresponding to plurality of C-arm position based on plurality of receiver navigation information.

20. The non-transitory computer readable medium of claim 18, wherein the routine for estimating receiver navigation failure information comprising: a routine for restoring the receiver navigation failure information based on a co-ordinate transformation using the transmitter navigation information, C-arm position and the calibrated receiver navigation information.

* * * * *